US 6,654,113 B2

(12) United States Patent
Fukazawa et al.

(10) Patent No.: US 6,654,113 B2
(45) Date of Patent: Nov. 25, 2003

(54) SURFACE INSPECTION APPARATUS (75) Inventors: Kazuhiko Fukazawa, Misato (JP); Takeo Oomori, Hachioji (JP)

(73) Assignee: Nikon Corporation, Tokyo (JP)

( * ) Notice: Subject to any disclaimer, the term of this patent is extended or adjusted under 35 U.S.C. 154(b) by 97 days.

(21) Appl. No.: 09/950,074

(22) Filed: Sep. 12, 2001

(65) Prior Publication Data

US 2002/0060789 A1 May 23, 2002

(30) Foreign Application Priority Data

Sep. 13, 2000 (JP) ........................................ 2000-277805
Dec. 5, 2000 (JP) ........................................ 2000-370695

(51) Int. Cl.[7] .............................................. G01N 21/88
(52) U.S. Cl. ................. 356/237.4; 356/237.5; 356/237.2; 250/559.45
(58) Field of Search ........................... 356/237.1, 237.2, 356/237.3, 237.4, 237.5, 239.1, 239.3, 239.7; 250/559.01–559.49

(56) References Cited

U.S. PATENT DOCUMENTS

| 5,777,729 A | | 7/1998 | Aiyer et al. | |
| 6,097,483 A | * | 8/2000 | Komatsu | ................. 356/237.2 |
| 6,288,780 B1 | * | 9/2001 | Fairley et al. | ........... 356/237.1 |

FOREIGN PATENT DOCUMENTS

| JP | 07-027709 A | 1/1995 |
| JP | 08-075661 A | 3/1996 |
| JP | 10-239038 A | 9/1998 |
| JP | 10-325805 A | 12/1998 |
| JP | 10-339701 A | 12/1998 |
| JP | 11-051874 A | 2/1999 |
| JP | 2000-206050 A | 7/2000 |
| JP | 2000-206050 | * | 7/2000 |

OTHER PUBLICATIONS

U.S. patent application Ser. No. 09/578,711, Oomori et al., filed May 26, 2000.
U.S. patent application Ser. No. 09/836,185, Oomori et al., filed Apr. 18, 2001.
U.S. patent application Ser. No. 09/083,538, Tanaka, filed May 22, 1998.
U.S. patent application Ser. No. 09/481,503, Komatsu et al., filed Jan. 12, 2000.
U.S. patent application Ser. No. 09/462,279, Komatsu et al., filed Jul. 09, 1998.
U.S. patent application Ser. No. 09/781,957, Oomori et al., filed Feb. 14, 2001.
U.S. patent application Ser. No. 09/918,476, Oomori et al., filed Aug. 01, 2001.

* cited by examiner

Primary Examiner—Richard A. Rosenberger
Assistant Examiner—Vincent P. Barth
(74) Attorney, Agent, or Firm—Oliff & Berridge PLC (57) ABSTRACT

The surface inspection apparatus according to the present invention obtains images of a test piece by capturing images of the test piece with an image-capturing device while varying at least one apparatus condition (e.g., the wafer tilt angle) through apparatus condition adjustment and determines an optimal setting at which a surface inspection is to be conducted on the test piece based upon the images thus obtained. As a result, the optimal setting for the inspection can be accurately ascertained with ease even when the pitch of a pattern formed at the surface of the test piece is not known, thereby making it possible to perform a surface inspection while sustaining high levels of accuracy and efficiency at all times.

11 Claims, 5 Drawing Sheets

SURFACE INSPECTION APPARATUS

INCORPORATION BY REFERENCE

The disclosures of the following priority applications are herein incorporated by reference: Japanese Patent Application No. 2000-277805 filed Sep. 13, 2000 Japanese Patent Application No. 2000-370695 filed Dec. 5, 2000

BACKGROUND OF THE INVENTION

1. Field of the Invention

The present invention relates to an apparatus employed to conduct a surface inspection on a test piece such as a wafer during the process of manufacturing IC chips, liquid crystal display panels and the like.

2. Description of Related Art

Many different circuit patterns are stacked over a plurality of layers at a surface of a substrate such as a wafer to manufacture an IC chip or a liquid crystal display element panel. These circuit patterns are formed by stacking them one layer at a time on the wafer through a photolithography process or the like.

When manufacturing an IC chip, for instance, a resist is applied in a thin layer onto an oxide film formed at a surface of a wafer (substrate) and then the resist layer is exposed with a circuit pattern at a reticle by an exposure apparatus. Next, the resist having been exposed is removed through development processing, thereby forming a pattern constituted of a resist layer achieving an identical form (or a similar reduced form) to the circuit pattern at the reticle. Subsequently, after removing the exposed oxide film through etching, the remaining resist layer is removed to form a circuit pattern constituted of the oxide film layer at the surface of the wafer. An element such as a diode is formed through doping processing or the like implemented on the circuit pattern constituted of the oxide film layer. While there is a degree of variance with regard to the manufacturing method depending upon the type of IC being manufactured, the process of forming a specific circuit pattern layer as described above is normally performed repeatedly to stack a plurality of circuit patterns over many layers on the wafer.

When circuit patterns are stacked over numerous layers on the wafer in this manner, a surface inspection is conducted to verify that no defect, abnormality or the like has occurred in the circuit pattern formed in each layer. This inspection may be implemented when, for instance, a circuit pattern constituted of the resist layer has been formed. If a surface defect, an abnormality or the like such as a deformation of the circuit pattern, inconsistency in the film thickness of the resist layer or a scar is detected during the inspection, reclaim processing is implemented for this circuit pattern layer. Namely, the resist is stripped and then a new resist layer is applied and exposed.

If a defect, an abnormality or the like occurs at any of the circuit patterns when manufacturing an IC chip or the like by stacking the circuit patterns over multiple layers on the wafer, the acceptability of the IC chip as a product is compromised. For this reason, it is crucial to conduct an inspection to detect such defects, abnormalities and the like, i.e., to conduct a wafer surface inspection.

The surface inspections proposed in the related art include an inspection in which various types of inspection illuminating light are irradiated on the test piece (wafer) surface from different angles and the light reflecting at the test piece is directly observed visually by the inspector as the test piece is rotated or tilted.

Such an inspection method is generally referred to as a macro inspection. When a macro inspection is implemented through visual observation by the inspector, there is a risk of inconsistency manifesting in the inspection results due to varying judgment criteria, skills and the like among individual inspectors. In addition, the onus placed on the inspector is significant. Accordingly, the possibility of automating macro inspections has been examined and various automatic macro inspection apparatuses have been proposed. For instance, there is an apparatus that performs an automatic surface inspection by irradiating inspection illuminating light onto a surface of a test piece, receiving the diffracted light from a repetitive pattern formed at the surface of the test piece with an image-capturing device to take in a diffracted image and performing image-processing on the diffracted image.

However, in the surface inspection apparatus in the related art, the optimal settings cannot be automatically selected for the apparatus conditions (the illuminating light incident angle, the tilt angle of the test piece substrate, the wavelength of the illuminating light, the position at which the light exiting the test piece and entering the image-capturing device is received and the like) when capturing a diffracted image based upon the diffracted light from the circuit pattern (repetitive pattern) on the surface of the test piece. The optimal settings in this context refer to conditions under which the direction along which the diffracted light originating from the repetitive pattern advances roughly matches the direction along which the optical axis of the light-receiving optical system that receives the diffracted light extends and, in other words, they are conditions under which a diffracted image that is good enough to enable a surface inspection is obtained.

The optimal settings for the apparatus conditions change in correspondence to the pitch of the repetitive pattern formed on the test piece. Thus, the apparatus conditions must be adjusted in correspondence to the pitch of the repetitive pattern. However, in reality, the inspectors are often not informed of the design value set for the repetitive pattern pitch. Accordingly, in the surface inspection apparatus in the related art, the diffracted image of the test piece is displayed on the monitor and the inspector selects the optimal settings for the apparatus conditions by checking the diffracted image on the monitor. However, this method poses a problem in that it is not always easy for the inspector to accurately judge the optimal apparatus conditions and thus, the inspector must have significant skills and experience.

SUMMARY OF THE INVENTION

An object of the present invention is to provide a surface inspection apparatus capable of determining the optimal apparatus conditions under which a defect inspection is to be performed and thus conducting a highly reliable surface inspection even when the pitch of a pattern at the surface of a test piece is not known.

The surface inspection apparatus according to the present invention comprises an illuminating device that illuminates a test piece having a plurality of repetitive patterns with different pitches formed at a surface thereof, an image-capturing device that captures an object image based upon diffracted light originating from the test piece, a condition control device that sets or changes an apparatus condition under which the object image is captured with the image-capturing device and a condition determining device that takes in images of object images, each captured by the image-capturing device every time the apparatus condition is changed by the condition control device and determines an optimal setting for the apparatus conditions for inspecting the patterns based upon the images thus taken in. The condition determining device takes in images of object images based upon diffracted light fluxes from the individual repetitive patterns with different pitches and determines the optimal settings for the apparatus condition in correspondence to the individual repetitive patterns.

A plurality of optimal settings may be determined in correspondence to the plurality of repetitive patterns with different pitches. Alternatively, a single optimal setting may be determined based upon a specific parameter.

The surface inspection apparatus may further comprise a storage device that stores in memory an object image captured under the optimal settings determined by the condition determining device and a defect detection device that reads out the image stored in the storage device and detects a defect in a pattern formed at the test piece based upon the image thus read out.

The surface inspection apparatus may further comprise a storage device that stores in memory the optimal settings determined by the condition determining device so that when inspecting a test piece other than the test piece used to determine the optimal settings, the condition control device reads out the optimal settings from the storage device to set the apparatus conditions in conformance to the optimal settings thus read out.

The condition determining device may select as optimal settings the apparatus conditions under which an object image achieving a highest brightness value among a plurality of object images captured by varying the apparatus conditions has been captured, or it may perform quadratic differentiation on the change occurring in the highest brightness among the object images each obtained every time the apparatus conditions are changed to select the apparatus conditions under which a brightness peak value is achieved as optimal settings.

The apparatus conditions is constituted of at least one of; the angle of incidence of the illuminating light irradiated by the illuminating device onto the test piece, the angle at which the test piece is mounted, the wavelength of the illuminating light and the position at which the light exiting the test piece and entering the image-capturing device is received.

The plurality of repetitive patterns with varying pitches formed at the surface of the test piece are constituted of transfer patterns formed by exposing an original pattern with an exposure apparatus, with a plurality of transfer patterns exposed on the surface of the test piece under identical exposure conditions. This enables the surface inspection apparatus according to the present invention to capture object images based upon diffracted light fluxes originating from the individual repetitive patterns with respect to a pair of the transfer patterns formed at positions distanced from each other at the surface of the test piece with the image-capturing device, to determine the optimal settings for the individual repetitive patterns based upon the captured images with the condition determining device to compare the optimal settings corresponding to the pair of transfer patterns for each repetitive pattern and to select the optimal settings corresponding to one of the repetitive patterns.

Alternatively, the surface inspection apparatus may capture object images based upon diffracted light fluxes originating from the individual repetitive patterns with respect to a pair of the transfer patterns formed at positions close to each other at the surface of the test piece with the image-capturing device, determine the optimal settings for the individual repetitive patterns based upon the captured images with the condition determining device, compare the optimal settings corresponding to the pair of transfer patterns for each repetitive pattern and select the optimal settings corresponding to one of the repetitive patterns.

The image-capturing device is constituted of a two-dimensional image-capturing element having a plurality of pixels, and the condition determining device may set the brightness value corresponding to each pixel and the number of pixels as the specific parameter. In this case, the condition determining device may store in memory a plurality of tilt angles corresponding to the highest level of brightness achieved in the object images captured by the image-capturing device to select one tilt angle among the plurality of tilt angles based upon the specific parameter. Alternatively, the condition determining device may ascertain the number of pixels achieving brightness values equal to or higher than a predetermined brightness value and the average brightness values among the pixels at varying tilt angles to select the optimal tilt angle based upon the number of pixels and the average pixel brightness values thus ascertained.

The image-capturing device is constituted of a two-dimensional image-capturing element having a plurality of pixels, and the condition determining device may store in memory a plurality of tilt angles corresponding to the highest level of brightness in an object image captured by the image-capturing device to select a plurality of optimal settings by determining the order of priority among the plurality of tilt angles based upon the brightness values at the individual pixels and the number of pixels.

DETAILED DESCRIPTION OF PREFERRED EMBODIMENTS (First Embodiment)

Figure 1:
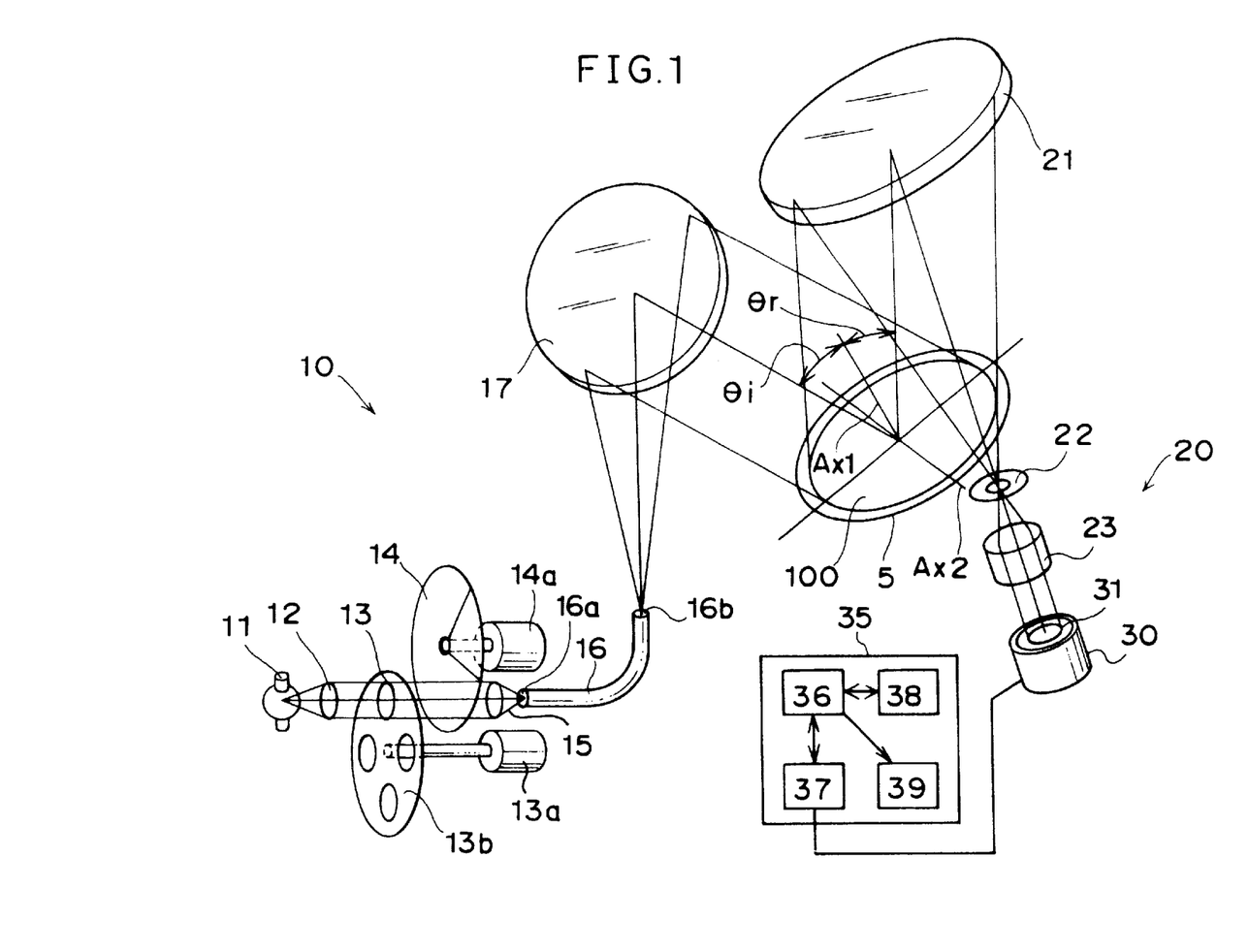
FIG. 1 is a schematic diagram illustrating the structure achieved in an embodiment of the surface inspection apparatus according to the present invention.

The following is an explanation of an embodiment of the surface inspection apparatus according to the present invention, given in reference to the drawings. FIG. 1 shows the structure assumed in an embodiment of the surface inspection apparatus according to the present invention. The surface inspection apparatus includes a holder 5 that holds a wafer 100 placed on it, and wafer 100 delivered by a delivery device (not shown) is placed onto the holder 5 and is securely held onto the holder 5 through vacuum hold-down. The holder 5 is allowed to rotate around an axis Ax1 extending perpendicular to the surface of the securely held wafer 100 (to rotate within the wafer plane) and is also allowed to tilt around an axis Ax2 passing through the center of an illuminating system concave mirror 17 and the center of the wafer 100.

The surface inspection apparatus further includes an illuminating optical system 10 that irradiates inspection illuminating light onto the surface of the wafer 100 securely held by the holder 5, a condenser optical system 20 that condenses reflected light, diffracted light and the like from the wafer 100 irradiated by the inspection illuminating light, a CCD camera 30 (an image-capturing device) that detects an image of the surface of the wafer 100 by receiving the light condensed by the condenser optical system 20 and the like.

The illuminating optical system 10 is provided with a discharge light source 11 such as a metal halide lamp, and a collector lens 12 that condenses an illuminating light flux emitted by the discharge light source 11, the wavelength selecting filter 13 that achieves a wavelength selection by allowing the illuminating light flux having been condensed by the collector lens 12 to be transmitted, a neutral density filter 14 that performs light modulation and an input lens 15. The illuminating light flux having been transmitted through the filters 13 and 14 becomes focused through the input lens 15 and the focused illuminating light is guided into one end 16a of a fiber 16.

The wavelength selecting filter 13 is provided within a disk (turret) 13b having a switching drive mechanism 13a and the wavelength selecting filter 13 selected from various types of filters 13 is used. For instance, an interference filter that allows only light with a specific wavelength such as a g-beam (with a wavelength of 436nm) or an i-beam (with a wavelength of 365 nm) to be transmitted, a band pass filter that allows light within a specific wavelength band to be transmitted, a sharp cut filter that allows only light having a wavelength greater than a specific wavelength to be transmitted or the like may be selected as necessary for use. The neutral density filter 14, which is constituted of a disk-shaped filter at which the quantity of transmitted light sequentially changes in correspondence to the rotational angle, is controlled by a rotation drive mechanism 14a to rotate over a specific angle to control the quantity of the transmitted light.

The illuminating optical system 10 is further provided with the illuminating system concave mirror 17, which receives a divergent light flux emitted from another end 16b of the fiber 16. The illuminating system concave mirror 17 is provided over a distance substantially matching the focal length of the illuminating system concave mirror 17 from the other end 16b of the fiber 16. As a result, the illuminating light guided into the one end 16a of the fiber 16 and diverged from the other end 16b of the fiber 16 to be irradiated on the illuminating system concave mirror 17 becomes a parallel light flux at the illuminating system concave mirror 17 and is then irradiated onto the surface of the wafer 100 held by the holder 5. The illuminating light flux irradiated onto the surface of the wafer 100 at this time achieves an angle $\theta i$ relative to the axis Ax1 (vertical axis) perpendicular to the surface of the wafer 100. The illuminating light flux having been irradiated on the wafer 100 exits the wafer 100 at an angle $\theta r$ relative to the axis Ax1 (vertical axis). The relationship between the incident angle $\theta i$ and the exiting angle $\theta r$ can be adjusted by tilting the holder 5 around the axis Ax2. Namely, the angle at which the wafer 100 is mounted can be varied by tilting the holder 5 to adjust the relationship between the incident angle $\theta i$ and the exiting angle $\theta r$.

The light exiting the surface of the wafer 100 (the diffracted light in this example) is condensed at the condenser optical system 20. The condenser optical system 20 includes a condenser system concave mirror 21 facing opposite the direction extending by achieving the angle $\theta r$ relative to the vertical axis Ax1, an aperture 22 provided at the position at which light is condensed at the condenser system concave mirror 21 and an image-forming lens 23 provided to the rear of the aperture 22. To the rear of the image-forming lens 23, the CCD camera 30 is provided. The lens 23 forms an image of the exiting light (nth-order diffracted light) having been condensed at the condenser system concave mirror 21 and constricted through the aperture 22 at a CCD image-capturing element (image device) 31 of the CCD camera 30. As a result, a diffracted image of the surface of the wafer 100 is formed at the CCD image-capturing element 31.

The CCD image-capturing element 31 generates an image signal through photoelectric conversion implemented on image of the surface of the wafer formed at its image receiving surface and provides the image signal thus generated to an image processing inspection device 35. The image processing inspection device 35 includes a control unit 37, a condition determining unit 38 that determines the optimal tilt angle for the wafer 100, a defect detection unit 39 that detects a defect at the wafer 100 and a memory (storage device) 36.

The control unit 37 implements control on the switching operation performed by the switching drive mechanism 13a to select a wavelength selecting filter 13, the rotation control on the neutral density filter 14 rotated by the rotation drive mechanism 14a, the control of the rotation of the holder 5 around the vertical axis Ax1, the control of the extent of the tilt of the holder 5 around the tilt axis Ax2 and the like. In addition, the control unit 37 converts the image of the wafer 100 obtained from the CCD image-capturing element 31 to a digital image with a predetermined bit-length (8-bit).

The digital image provided by the control unit 37 and the apparatus condition (the tilt angle) under which the image of the wafer 100 was obtained are stored in the memory 36. The stored digital image is output to the condition determining unit 38 when determining the optimal tilt angle for the wafer 100 and is output to the defect detection unit 39 when detecting a defect at the wafer 100. When determining the optimal tilt angle for the wafer 100, the control unit 37 takes in images of the wafer 100 by varying the tilt angle. The images of the wafer 100 at the varying tilt angles are converted to digital images as described above and are sequentially stored into the memory 36.

The condition determining unit 38 sequentially takes in the digital images of the wafer 100 stored in the memory 36, ascertains the highest brightness values (or the average brightness values) of the individual digital images and determines the optimal tilt angle $\phi s$ for the wafer 100 based upon the highest brightness values.

The defect detection unit 39 performs image processing on a digital image of the wafer 100 taken in from the memory 36, monitors the light quantity of the image and identifies a defect such as an inconsistency in the film thickness at the wafer 100, an abnormal pattern shape or a scar based upon the contrast of the image.

Since a cyclically repeated line array circuit pattern is formed at the surface of the wafer 100 constituting the test piece, the lines constituting the circuit pattern are arrayed in repetition at the surface of the wafer 100. Accordingly, with p representing the repetition pitch of the lines constituting the circuit pattern and λ representing the wavelength of the illuminating light, the nth-order diffracted light from the wafer 100 can be condensed at the CCD camera 30 via the condenser optical system 20 by tilting the holder 5 at a tilt angle T formed by the surface of the wafer 100 satisfying the following equation (1). The surface is inspected to determine whether or not any defect is present based upon the image of the surface of the wafer 100 obtained at the CCD image-capturing element 31 by receiving the nth-order diffracted light in this manner.

$$\sin(\theta i - T) - \sin(\theta r + T) = n \cdot \lambda / p \quad (1)$$

In equation (1), θi and θr represent the values of the incident angle and the exiting angle before the tilt angle T is changed (tilt angle T=0), i.e., the initial values for the incident angle and the exiting angle. The incident angle (θi−T) and the exiting angle (θr+T) of the nth-order diffracted light after the tilt angle T is changed assume positive values along the angular direction taken toward the entry side relative to the normal line Ax1 to the surface of the wafer 100 and assume negative values along the angular direction taken toward the opposite side. The tilt angle T may assume a value of 0°, for instance, when the holder 5 is in a horizontal state, assume a positive value along the angular direction toward the entry side and a negative value along the angular direction taken toward the exiting side. The diffraction order n assumes a positive value along the angular direction taken toward the entry side relative to the 0-order light (specular reflected light) at n=0 and assumes a negative value along the angular direction taken toward the opposite side.

As described above, the image signal representing the image of the surface of the wafer 100 captured by the CCD image-capturing element 31 is provided to the image processing inspection device 35. The image processing inspection device 35 engages in pattern matching of the image of the surface of the wafer 100 obtained through the image signal provided by the CCD image-capturing element 31 and an image of the surface of an acceptable wafer product stored in memory in advance (inspection reference image) or it determines whether or not there is any difference between the characteristics of the image of the surface of the wafer 100 and the characteristics of a pre-learned inspection reference image. If a defect attributable to defocusing such as inconsistency in the film thickness, an abnormal pattern shape or a scar is present at the wafer 100 undergoing the inspection, a difference in the contrast manifesting at the defective area from the inspection reference image or a difference in the image characteristics from the inspection reference image is detected and thus, the presence of the defect is detected.

In order to detect a defect at the wafer 100 with a high degree of reliability, the apparatus conditions must be set so as to allow the diffracted light from the wafer 100 to be condensed at the CCD camera 30 via the condenser optical system 20 when inspection illuminating light is irradiated onto the surface of the wafer 100 held by the holder 5 from the illuminating optical system 10. These apparatus conditions may be, for instance, the wavelength λ of the illuminating light irradiated on the wafer 100, the incident angle θi of the illuminating light, the exiting angle θr of the light exiting the wafer 100 to enter the condenser optical system 20 and the tilt angle T of the wafer 100 (the holder 5). The surface inspection should be conducted by setting such apparatus conditions so as to satisfy equation (1) for the pitch p of the circuit pattern formed at the surface of the wafer 100.

While the apparatus condition only need to be set so as to satisfy equation (1) as long as the pitch p of the circuit pattern is known, the pitch p is often unknown. The following is an explanation of a surface inspection apparatus and an inspection method that make it possible to ascertain the apparatus condition which satisfies equation (1), i.e., to ascertain the optimal apparatus condition even when the pitch p of the circuit pattern is not known.

Determining Optimal Setting

Figure 2:
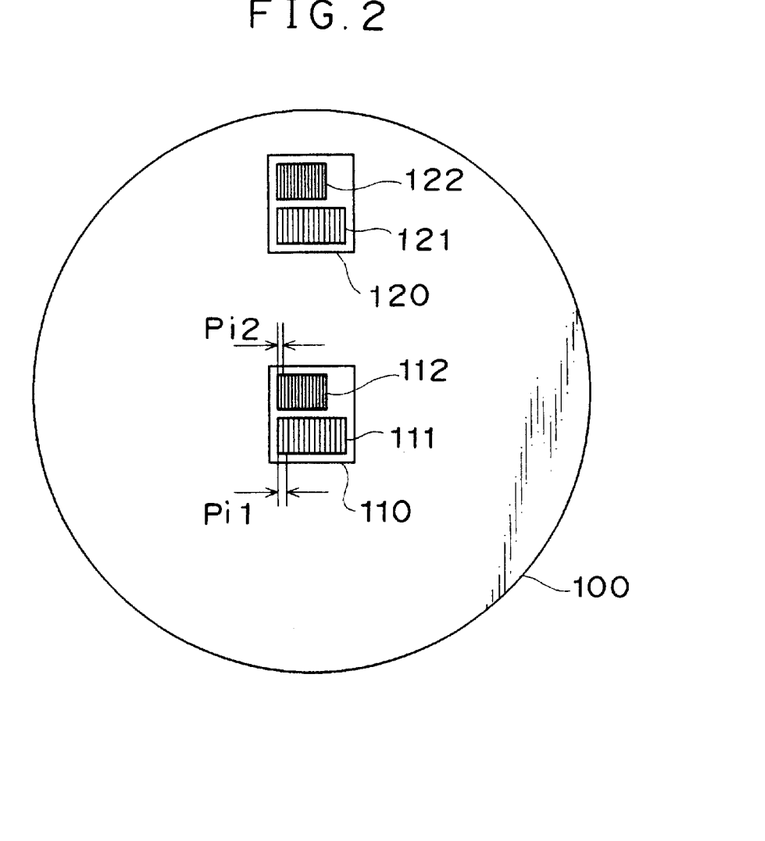
FIG. 2 is a plan view of an example of patterns formed at the surface of a wafer constituting the inspection target of the surface inspection apparatus according to the present invention.

FIG. 2 schematically illustrates an example of a circuit pattern (transfer pattern) that may be formed at the surface of the wafer 100. At the surface of the wafer 100, circuit patterns are exposed and formed side-by-side onto each of a plurality of shot areas by an exposure apparatus. While two shot areas 110 and 120 are shown as examples in FIG. 2, numerous shot areas are formed side-by-side in reality.

FIG. 2 shows a first shot area 110 set close to the center of the wafer 100 and a second shot area 120 set at the periphery. In the first shot area 110, a first pattern 111 and a second pattern 112 with different repetition pitches are formed whereas in the second shot area 120, a first pattern 121 and a second pattern 122 with different repetition pitches are formed. The wafer 100 is utilized to determine the optimal apparatus condition. It is to be noted that the entire pattern formed through exposure at each shot area is referred to as a transfer pattern. For instance, a transfer pattern constituted of the first pattern 111 and the second pattern 112 with different repetition pitches is formed through exposure at the first shot area 110.

The patterns (transfer patterns) in the individual shot areas formed through exposure at the surface of the wafer 100 are formed by exposing a pattern (original pattern) on a single reticle (mask) under identical conditions with a single exposure apparatus. Accordingly, identical patterns are formed through exposure within the first and second shot areas 110 and 120. The first patterns 111 and 121 in the two shot areas are constituted of identical patterns with the same pitch p1 and the second patterns 112 and 122 in the two shot areas are constituted of identical patterns achieving the same pitch p2.

When conducting an inspection by employing the surface inspection apparatus shown in FIG. 1 on this wafer 100, it should be assumed that there are two sets of apparatus conditions for capturing a wafer surface image with the CCD camera 30 by using diffracted light originating from the wafer 100, since the exiting angle of the diffracted light originating from the first patterns 111 and 121 with the pitch p1 is different from the exiting angle of the diffracted light originating from the second patterns 112 and 122 with the pitch p2. In the embodiment, by assigning the tilt angle T of the wafer 100 (the holder 5) alone as a variable and fixing all the other apparatus conditions among the plurality of apparatus conditions listed earlier, the two conditions corresponding to the tilt angle T are ascertained.

Figure 5:
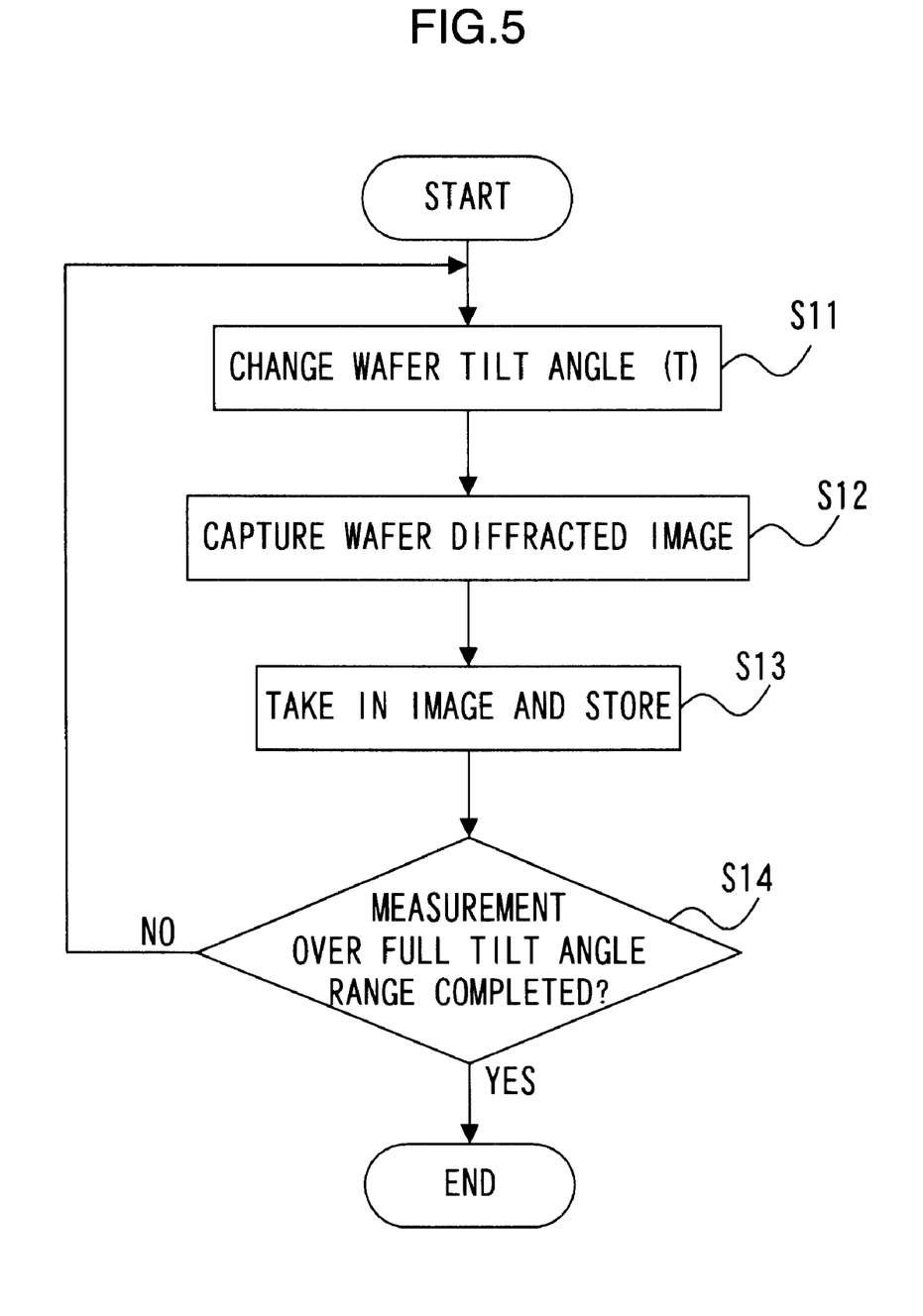
FIG. 5 is a flowchart of the image-capturing procedure and the image intake procedure implemented at the control unit of the surface inspection apparatus according to the present invention.
Figure 6:
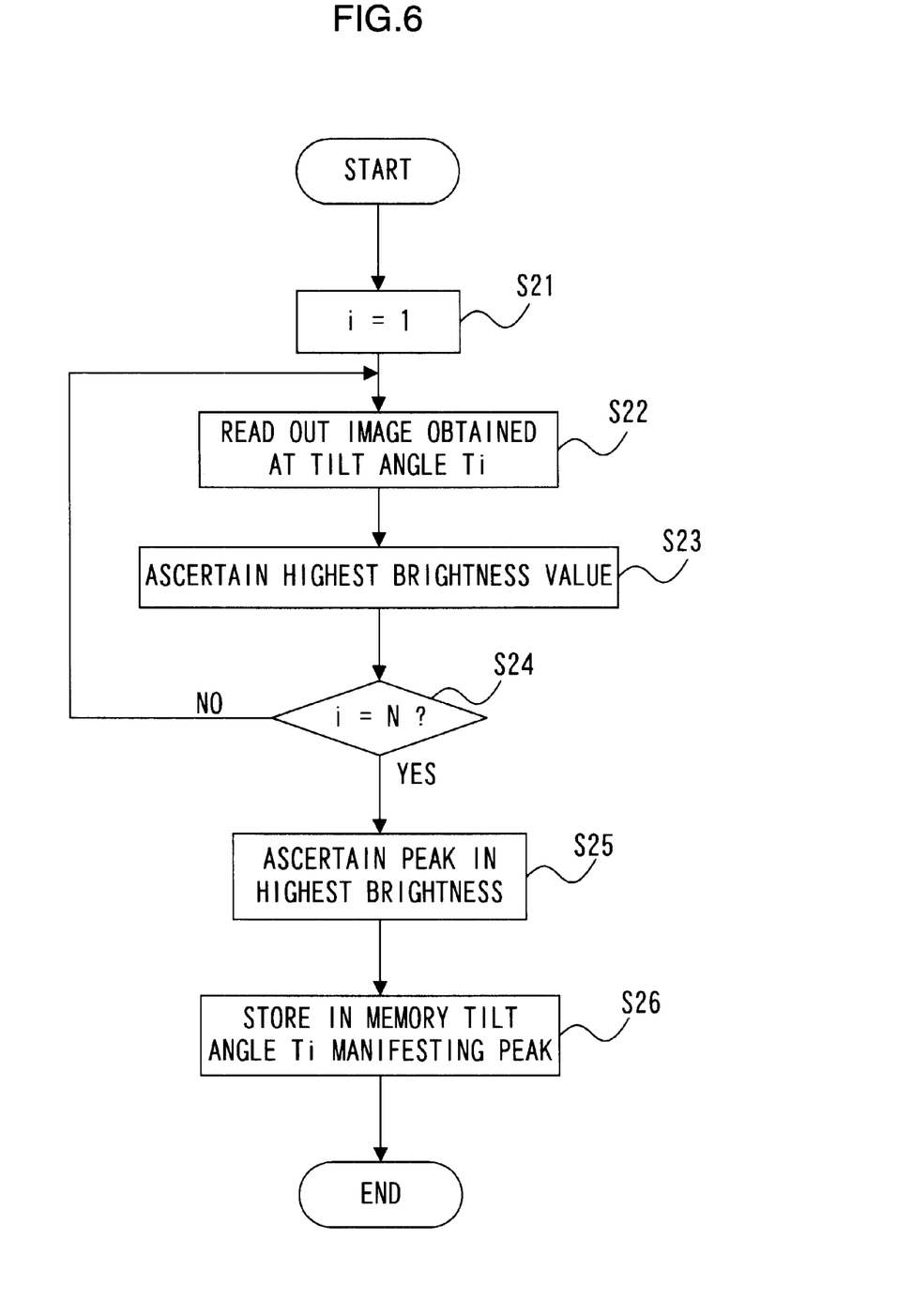
FIG. 6 presents a flowchart of the procedure through which the optimal settings for an image inspection are determined in the surface inspection apparatus according to the present invention.

The following is an explanation of the operation of the surface inspection apparatus achieved in the first embodiment, given in reference to the flowcharts presented in FIGS. 5 and 6.

The inspection is started after the wafer 100 is placed and secured onto the holder 5 and as inspection illuminating light achieving a predetermined wavelength λ from the illuminating optical system 10 is irradiated onto the surface of the wafer 100. The control unit 37 changes the tilt angle T of the wafer 100 by controlling the holder 5 (step S11) and takes in a two-dimensional image of an image of the wafer surface captured by the CCD camera 30 (step S12). During this operation, a plurality of captured images corresponding to different tilt angles T and the corresponding apparatus conditions (tilt angles) are stored in the memory 36 (step S13). Images are captured by the CCD camera 30 over the entire surface of the wafer 100. More specifically, since the range over which the tilt angle varies is set so as to capture images over an incident angle range of 20°~75° with regard to the inspection illuminating light from the illuminating optical system 10, the operation to capture images of the entire surface of the wafer 100 at the various tilt angles is completed when the image intake over the full range of the tilt angle variance is completed (step S14).

Now, the processing implemented after the completion of the image-capturing operation for the entire surface performed at the different tilt angles is explained in reference to the flowchart in FIG. 6. The condition determining unit 38 ascertains the highest brightness value (or the average brightness value) of each image corresponding to one of the tilt angles T based upon the information of the plurality of two-dimensional images (the entire image of the wafer 100) stored in the memory 36. In more specific terms, the condition determining unit 38 reads out the image captured and stored as described above at each tilt angle Ti (i=1~N) (step S22) and ascertains the highest brightness value of each image (step S23) The processing for determining the highest brightness values of the individual image is implemented for all the images obtained through the image-capturing operation (steps S21~S24).

The relationship of the highest brightness value corresponding to the tilt angle T ascertained through the processing procedure described above is shown in FIG. 3. As FIG. 3 indicates, the highest brightness value peaks at a tilt angle T=t1 and a tilt angle T=t2. The condition determining unit 38 engages in processing for quadratically differentiating the waveform in FIG. 3 in order to accurately detect the peak positions of the highest brightness value, thereby ascertaining turning points of the highest brightness value (step S25). The results of the quadratic differentiation are shown in FIG. 4. As FIG. 4 shows, the highest brightness value peaks at the tilt angle t1 and the tilt angle t2.

In order to satisfy equation (1), $\sin(\theta i-t)-\sin(\theta r+T)$ must assume a smaller value as the pitch p of the pattern on the wafer becomes larger if the wavelength $\lambda$ of the illuminating light is constant. This is achieved by setting the tilt angle T to a positive value (along the direction in which the incident angle $\theta i-T$ is reduced or the direction in which the exiting angle $\theta r+T$ is increased).

Figure 3:
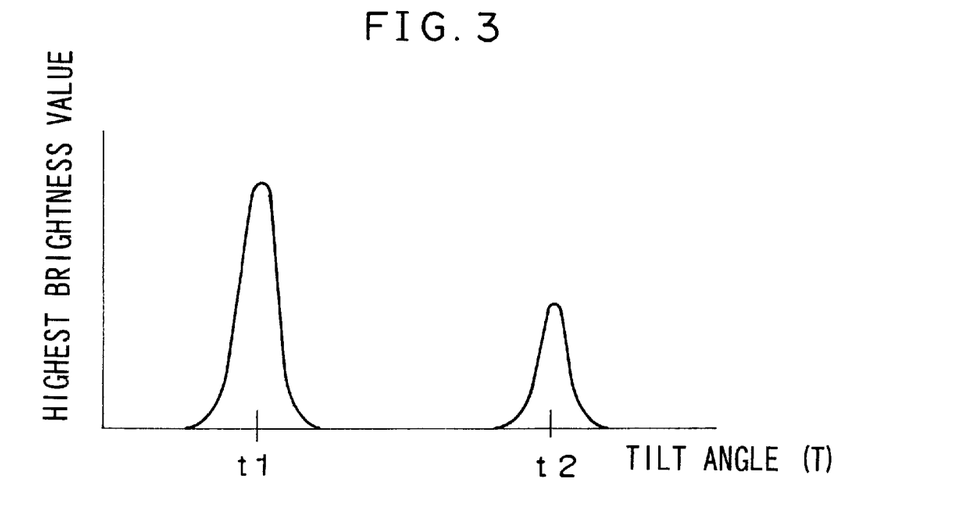
FIG. 3 presents a graph of the relationship between the tilt angle and the highest brightness level manifesting when the surface of the wafer shown in FIG. 2 is inspected.
Figure 4:
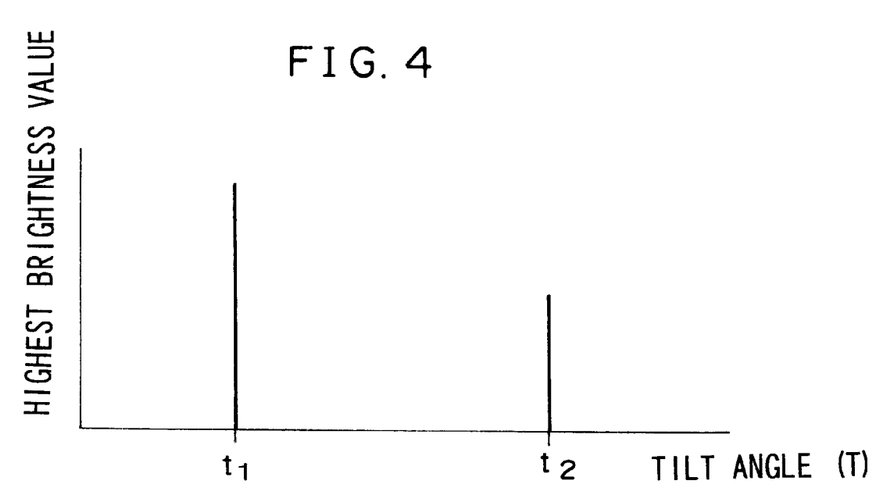
FIG. 4 presents a graph showing the results of the quadratic differentiation performed on the waveform presented in FIG. 3.

Thus, it is determined that the smaller tilt angle t1 among the tilt angles t1 and t2 at which the two highest brightness value peaks manifest as shown in FIG. 3 is determined to correspond to the diffracted light from the first patterns 111 and 121 (the patterns with the larger pitch) and the larger tilt angle t2 is determined to correspond to the diffracted light from the second patterns 112 and 122 (the patterns with the smaller pitch). In other words, the tilt angle t1 constitutes the apparatus condition for receiving the diffracted light from the first patterns 111 and 121 at the CCD camera 30. Likewise, the tilt angle t2 constitutes the apparatus condition for receiving the diffracted light from the second patterns 112 and 122. These apparatus conditions are stored together with other apparatus conditions in the memory 36 (step S26).

Even if two peaks manifest as described above, the surface inspection apparatus does not need to identify which patterns each peak corresponds to. As long as it is recognized that there are patterns with two different pitches, an inspection can be performed through the method described below.

The defect detection unit 39 reads the digital images of the wafer 100 corresponding to the tilt angles t1 and t2 at which the highest brightness value indicates peak values from the memory 36. The defect detection unit 39 performs image processing on the individual digital images that have been read, monitors the light quantities of the images and identifies a defect present at the wafer 100 based upon the contrast in the images. Thus, defects can be detected for the two different patterns. By identifying the patterns corresponding to the different tilt angles at which the highest brightness value peaks as described above, it is possible to specify the pattern at which the defect is present.

Variation

It is to be noted that in the explanation of the operation given above, the optimal settings are determined first, and then the images of the wafer obtained under the optimal settings are read out from the memory 36 to be used for the defect detection. However, the wafer 100 may be used only to determine the apparatus conditions. Namely, a given wafer may be used to determine the optimal apparatus conditions, and another wafer having identical patterns formed therein is inspected under the optimal apparatus conditions. In such a case, it is not necessary to store the images of the wafer used for determining the optimal apparatus conditions in the memory 36 once the optimal apparatus conditions are determined, and only the optimal apparatus conditions that has been determined alone need to be stored in the memory.

The other wafer should be inspected through the following method after the optimal apparatus condition is determined.

Surface Inspection At Optimal Settings

First, the wafer to undergo the inspection is delivered by the delivery device (not shown) to the holder 5. The holder 5 securely holds the wafer through vacuum holddown. Then, while inspection illuminating light with a predetermined wavelength $\lambda$ is irradiated from the illuminating optical system 10 onto the surface of the wafer, the inspection is performed. The control unit 37 reads the optimal apparatus conditions stored in memory 36. If two optimal apparatus conditions (tilt angles) have been determined as described earlier, the two sets of optimal apparatus conditions (the tilt angles t1 and t2) are read. Then, the control unit 37 controls the holder 5 to set the tilt angle to t1. The control unit 37 takes in the entire image of the wafer captured by the CCD camera 30 at this setting, converts the image to a digital image and stores the converted image into the memory 36.

The defect detection unit 39 reads the digital image from the memory 36 and also monitors the quantity of light in the image to identify a defect at the wafer 100 based upon the contrast of the image. Likewise, the control unit 37 conducts an inspection by controlling the holder 5 to set the tilt angle to t2. As a result, defects can be detected in the two different patterns on the wafer.

(Second Embodiment)

If there are two optimal apparatus conditions, an inspection is performed under the two conditions in the first embodiment. In the second embodiment, on the other hand, an inspection is conducted by selecting one set of optimal apparatus conditions among the plurality of sets of optimal apparatus conditions. The method adopted in the second embodiment is explained below.

In the second embodiment, too, the surface inspection apparatus shown in FIG. 1 is employed to inspect the wafer 100 having the circuit patterns formed as shown in FIG. 2, as in the first embodiment. In this embodiment, too, the inspection is performed after the wafer 100 is placed and secured onto the holder 5 and as inspection illuminating light with a predetermined wavelength λ from the illuminating optical system 10 is irradiated onto the surface of the wafer 100. The control unit 37 varies the tilt angle T of the wafer 100 by implementing control on the holder 5. The CCD camera 30 captures an image of the wafer surface at each of the different tilt angles T at which the wafer 100 is tilted and takes in the two-dimensional image. Images are captured by the CCD camera 30 over the entire surface of the wafer 100. During the operation, the plurality of captured images corresponding to the various tilt angles T and the corresponding apparatus conditions (tilt angles) are stored in the memory 36.

The condition determining unit 38 ascertains the highest brightness value (or the average brightness value) achieved in each image corresponding to one of the various tilt angles T based upon the information of the plurality of two-dimensional images (the entire image of the wafer 100) having been stored in the memory 36. The tilt angles T=t1 and T=t2 at which the highest brightness value peaks are determined based upon the relationship of the highest brightness value to the tilt angle T (e.g., the relationship shown in FIG. 3) ascertained through the processing procedure described earlier and these tilt angle settings are stored as optimal settings in the memory 36.

The condition determining unit 38 reads out the optimal settings (tilt angles t1 and t2) stored in the memory 36. The condition determining unit 38 first reads out the image information corresponding to the tilt angle t1 from the memory 36 to determine the number of pixels manifesting brightness equal to or higher than a predetermined brightness level (pixel value). The area corresponding to the number of pixels thus ascertained is assumed to be the area over which the first pattern was formed through exposure. The condition determining unit 38 calculates the average brightness value among the pixels manifesting brightness equal to or higher than the predetermined brightness level and stores the number of pixels and their average brightness value into the memory 36.

Likewise, the image information corresponding to the tilt angle t2 is read out from the memory 36, the number of pixels manifesting brightness equal to or higher than the predetermined brightness level and the average brightness value among these pixels are ascertained as described above and they are stored into the memory 36. The areas corresponding to these pixels are assumed to be the areas over which the second patterns were formed through exposure.

Next, the condition determining unit 38 reads out the numbers of pixels and the average brightness values corresponding to the individual tilt angles that have been stored in memory and determines the ultimate optimal setting based upon these values. For instance, if the number of pixels corresponding to t1 is larger than the number of pixels corresponding to t2 (namely if it is assumed that the areas over which the first patterns were formed through exposure are larger) and the average brightness value among the pixels corresponding to t1 is high, the tilt angle t1 is determined to be the optimal setting. The ultimate optimal setting thus determined is then stored into the memory 36.

The present invention is not limited to the examples in the embodiments described above. For instance, a surface inspection may be conducted by setting a plurality of tilt angles based upon the number of pixels and the average brightness values with the surface inspection apparatus achieved in the second embodiment described above. In this case, the order of priority should be set forth with regard to the tilt angle settings based upon the two parameters, i.e., the number of pixels and the average brightness value. This order of priority is naturally set in the order starting with the largest number of pixels and the highest average brightness value. By conducting a surface inspection at the plurality of tilt angles and making an integrated judgment on the results of the inspection, the accuracy of the surface inspection can be improved.

What is claimed is:

1. A surface inspection apparatus comprising;
    an illuminating device that illuminates a test piece having a plurality of repetitive patterns with different pitches formed at a surface thereof;
    an image-capturing device that captures an object image based upon diffracted light originating from the test piece;
    a tilt angle changing device that changes a tilt angle of the test piece by controlling a holder that holds the test piece;
    a condition control device that executes a tilt angle changing operation in which the tilt angle changing device changes the tilt angle of the test piece plural times;
    a condition determining device that takes in object images, each captured by said image-capturing device every time the tilt angle is changed in the tilt angle changing operation and determines an optimal tilt angle based on the object images captured for each tilt angle change; and
    a memory that stores the optimal tilt angle determined by the condition determining device; wherein:
    the surface of the test piece is inspected with the optimal tilt angle stored in the memory.

2. A surface inspection apparatus according to claim 1, wherein:
    the condition determining device determines a plurality of optimal tilt angles, each corresponding to the plurality of repetitive patterns with different pitches formed at the surface of the test piece.

3. A surface inspection apparatus according to claim 1, further comprising:
    a control device that reads out the optimal tilt angle stored in the memory, controls the tilt angle changing device based upon the optimal tilt angle and controls the image-capturing device to capture an object image if the optimal tilt angle has been set; and
    a defect detection device that detects a defect in a pattern formed at the test piece based upon the object image having been captured.

4. A surface inspection apparatus according to claim 1, wherein:
    said condition determining device determines the optimal tilt angle under which an object image achieving a highest brightness value among the plurality of object images captured by varying the tilt angle has been captured.

5. A surface inspection apparatus according to claim 1, wherein:
    said condition determining device performs quadratic differentiation on a change occurring in the highest brightness in object images each obtained every time the tilt angle is changed to determine the optimal tilt angle under which a peak manifests in the brightness.

6. A surface inspection apparatus according to claim 1, further comprising:
    an other condition changing device that changes an angle of incidence of the illuminating light irradiated by the illuminating device onto the test piece, a wavelength of the illuminating light and a position at which the light exits the test piece and enters the image-capturing device, wherein:

the condition control device executes the tilt angle changing operation in which the tilt angle changing device and the other condition changing device control plural parameters.

7. A surface inspection apparatus according to claim 1, wherein:

the plurality of repetitive patterns with different pitches formed at the surface of the test piece are constituted of a transfer pattern formed by exposing an original pattern with an exposure apparatus, with a plurality of transfer patterns exposed on the surface of the test piece under identical exposure conditions.

8. A surface inspection apparatus according to claim 7, wherein:

said image-capturing device captures object images based upon diffracted light fluxes originating from individual repetitive patterns with respect to a pair of transfer patterns formed at positions distanced from each other at the surface of the test piece and said condition determining device determines the optimal tilt angles for each of the repetitive patterns based upon the captured images; and the optimal tilt angles corresponding to the pair of transfer patterns are compared for each repetitive pattern and the optimal tilt angle corresponding to one of the repetitive patterns is selected.

9. A surface inspection apparatus according to claim 7, wherein:

said image-capturing device captures object images based upon diffracted light fluxes originating from individual repetitive patterns with respect to a pair a transfer patterns formed at positions close to each other at the surface of the test piece and said condition determining device determines the optimal tilt angles for each of the repetitive patterns based upon the captured images; and the optimal tilt angles corresponding to the pair of transfer patterns are compared for each repetitive pattern and the optimal tilt angle corresponding to one of the repetitive patterns is selected.

10. A surface inspection apparatus according to claim 1, wherein:

the image-capturing device includes a two-dimensional image-capturing element having a plurality of pixels;

the memory stores a plurality of tilt angles at which highest brightness levels achieved in the object images captured by said image-capturing device are obtained for each repetitive pattern; and the condition determining device selects one tilt angle among the plurality of tilt angles based upon the number of pixels of the image-capturing element and the highest brightness levels.

11. A surface inspection apparatus according to claim 1, wherein:

said image capturing device is constituted of a two-dimensional image-capturing element having a plurality of pixels; and the memory stores a plurality of tilt angles at which highest brightness levels in the object images captured by said image-capturing device are obtained for each repetitive pattern; and the condition determining device selects a plurality of optimal tilt angles by determining an order of priority among the plurality of tilt angles based upon brightness values each corresponding to one of the pixels and the number of pixels.

* * * * *